United States Patent [19]

Dimacopoulos

[11] 4,173,604
[45] Nov. 6, 1979

[54] ENVIRONMENTAL CONTROL DISPENSER

[75] Inventor: Dimitrios A. Dimacopoulos, Redondo Beach, Calif.

[73] Assignee: Cline-Buckner, Inc., Cerritos, Calif.

[21] Appl. No.: 876,322

[22] Filed: Feb. 9, 1978

[51] Int. Cl.² ............................................. F02M 37/00
[52] U.S. Cl. ...................................... 261/30; 261/99; 261/104; 261/DIG. 17; 239/45
[58] Field of Search .................................. 239/44–51.5; 220/90.4, 90.6, 257, 270; 261/99, 104, 30, DIG. 17

[56] References Cited

U.S. PATENT DOCUMENTS

| 674,943 | 5/1901 | Clair | 239/44 |
| 1,123,036 | 12/1914 | Tiemann | 239/45 |
| 1,662,938 | 3/1928 | Richmond | 239/45 |
| 2,572,329 | 10/1951 | Foster | 239/45 |
| 2,828,953 | 4/1958 | Hartmann | 239/44 X |

Primary Examiner—John J. Love
Attorney, Agent, or Firm—Albert L. Gabriel

[57] ABSTRACT

A vapor generator for generating vapors from a vaporizable liquid concentrate such as a deodorant-fragrance concentrate and employable either with or without a fan dispenser. The vaporizable liquid is sealed within a receptacle having an openable top portion, such as a pull-top can, and a capillary action diaphragm is located under the top so as to be exposed when the top is opened. The vaporizable liquid is transported upwardly from the body of liquid to the diaphragm by capillary action membrane means extending from the top to the bottom of the receptacle, and then distributed by capillary action through the diaphragm and vaporized from the exposed surface thereof. A small pressure equalization port through the diaphragm equalizes the vapor pressure under the diaphragm to substantially atmospheric pressure so that such vapor pressure will not interfere with the capillary actions. The good vaporization rate control obtainable by this arrangement enables a combination of active and carrier ingredients to be used for the liquid which are substantially entirely vaporizable at rates corresponding to their proportions, for effective functioning of the vapor generator over a long operational life cycle.

21 Claims, 10 Drawing Figures

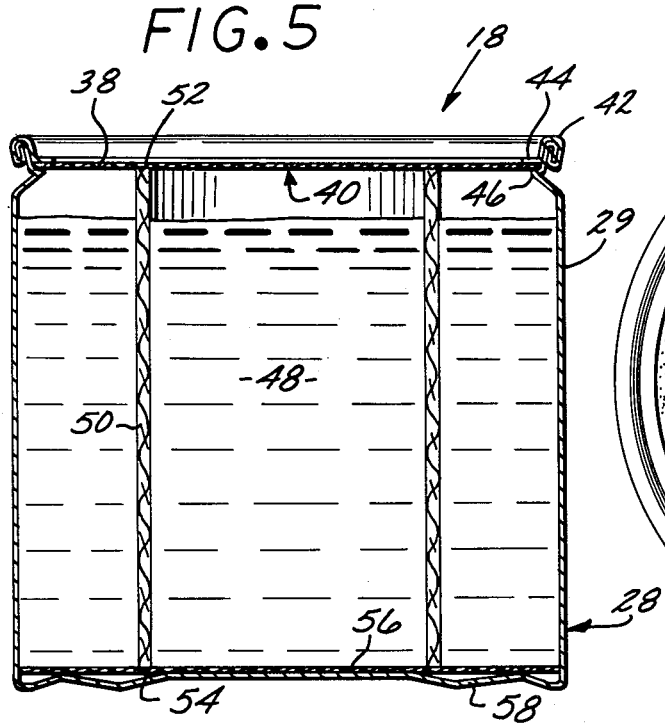
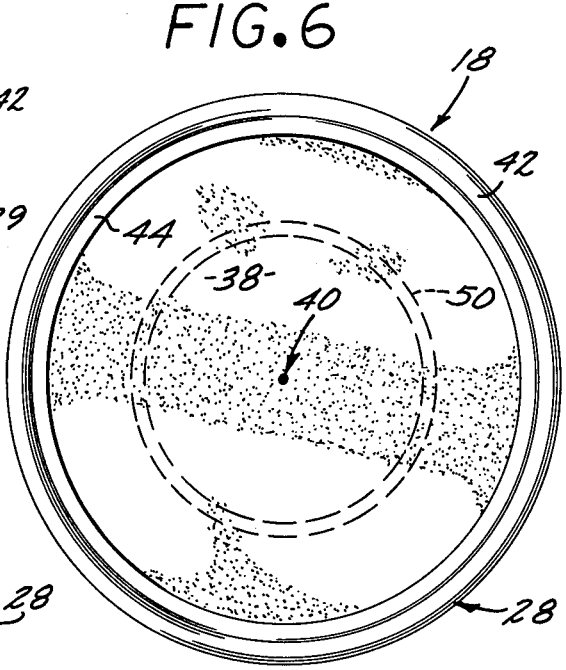
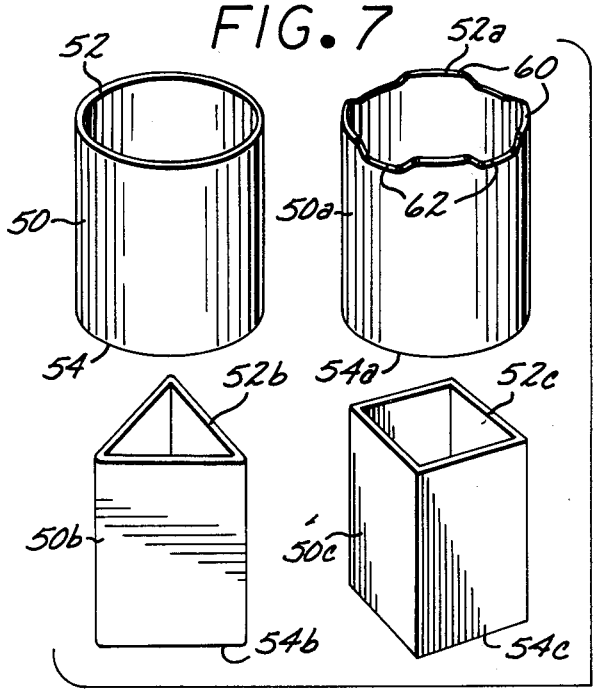
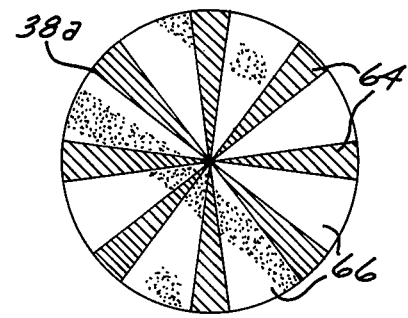
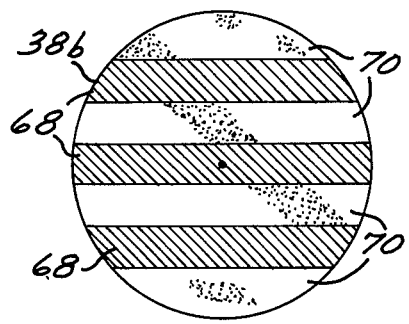
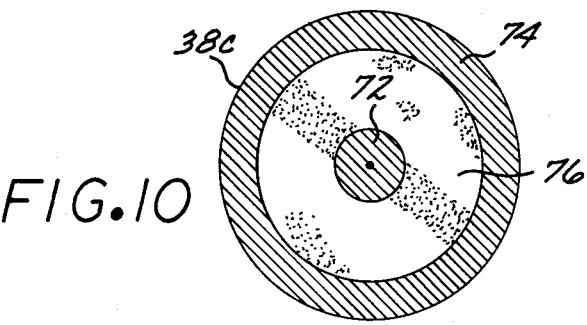

ENVIRONMENTAL CONTROL DISPENSER

BACKGROUND OF THE INVENTION

1. Field of the Invention

Vapor dispensers for environmental control, and particularly for dispensing vapors from a liquid deodorant-fragrance concentrate for counteracting or replacing undesirable odors.

2. DESCRIPTION OF THE PRIOR ART

The principal prior art type of vapor dispenser for dispensing vapors from a liquid deodorant-fragrance concentrate to counteract undesirable odors is a wick system wherein the liquid deodorant-fragrance concentrate is provided in a "pull tab" can, and a cotton of felt wick is provided separately from the can. The system is activated by pulling off the "pull tab" from the top of the can, and then folding over the cloth wick strip and pushing the wick into the can. The activated can with the wick in it is then usually placed inside of a fan dispenser, and the fan dispenser then hung high on a wall.

This prior art liquid wick system has a number of serious disadvantages, all of which are overcome by the present invention. A very basic problem associated with this liquid wick system is that it is an uncontrollable way of releasing the active ingredient, so that it is necessary that a large proportion of evaporation retardants be included in the liquid formulation. These evaporation retardants are substantially non-volatile hydrocarbons, and comprise up to 40% to 60% of the liquid formulation that is provided in the can. This relatively large proportion of non-volatile retardants in the formulation seriously reduces the amount of the active ingredient that is available in the dispenser, and despite the reduced rate of evaporation caused by the presence of the retardants, the active ingredient is still normally dispensed much too rapidly for the normal 30-day service interval of most route men who service this type of equipment in commercial establishments. Thus, typically prior art vapor generators of this liquid-wick type will be substantially completely depleted of their active ingredient in only about two weeks, or only about one half of the normal service interval for this type of equipment.

In addition to such basic efficacy problems with the liquid-wick type prior art vapor generator, it also presents the service man with some undesirable handling problems. Thus, manual insertion of the cloth wick after the top of the can has been opened presents an extra step in the activation of the device. During this activation step, not only does insertion of the wick tend to be messy, but there is a substantial likelihood of spilling some of the liquid deodorant-fragrance concentrate, and this can apply an undesirably concentrated odor to the area being serviced or to the service man's clothing. Next, the wick must be adjusted to the desired exposed height, and if the wick is too far out, the entire active ingredient within the can may be dispensed much too soon, while on the other hand if the wick is too far in, an inadequate concentration of the odor counteractant vapor will be dispensed in the area. After the vapor generator has been placed in a fan dispenser, it is then necessary for the service man to dispose the dispenser high on a wall as a safety measure, because of the opening at the top of the can which provides direct access to the strong liquid deodorant-fragrance concentrate in the can, and when reaching up high it is easy for the service man to spill some of the contents.

Then, when the service man returns to replace the depleted prior art liquid-wick type device, the remaining up to 40% to 60% of hydrocarbon retardant liquid in the can presents a substantial disposal problem. Again, spilling is likely when the service man removes the device from its high place on a wall. Generally, the service man is required to recap the can in some way in order to hold this substantial quantity of remaining liquid before the can may be discarded. The remaining contents of the can are flammable, and thereby present a danger of fire, and applicable regulations normally prevent the dumping of such hydrocarbons into sewers, so that the service man is normally required to transport the used cans with the retardant therein be some special disposal location.

SUMMARY OF THE INVENTION

In view of these and other problems in the art, it is an object of the present invention to provide a novel vapor generator and vapor generating method for dispensing vapors from a liquid concentrate which enables substantially all of the original liquid content of the vapor generator to vaporize, whereby a maximum quantity of the liquid concentrate is dispensed for the size of the dispenser, and there is substantially no liquid remaining in the vapor generator after a complete operational cycle thereof which would otherwise present disposal or handling problems.

Another object of the present invention is to provide a novel vapor generator and method of the character described for dispensing vapors from liquid concentrate wherein the vapor generator container after activation remains fully enclosed against any spillage whatsoever of its liquid contents during handling.

Another object of the invention is to provide a vapor generator and method of the character described which is activated by the simple expedient of opening up a pull-top can, at which time fully effective release of vapor commences, and wherein no further activation steps are required such as the usual folding and insertion of a cloth wick.

A further object of the invention is to provide a vapor generator and method of the character described which has a controllable, long-lasting operational life cycle which can be made to extend beyond the usual 30-day service interval for commercial vapor dispensing apparatus.

A further object of the invention is to provide a vapor generator and method which employs a novel capillary action made of operation to provide a generally constant degree of saturation of a vapor dispensing diaphragm, for good control of the dispensing rate and long operational life.

A still further object of the present invention is to provide a vapor generator and method of the character described wherein the liquid concentrate employed to provide the vapor is conducted by capillary action to and through an exposed vapor dispensing diaphragm, and wherein such diaphragm has a small pressure equalization port therethrough which prevents thermal vapor pressure buildup in the generator from interfering with the capillary action.

Yet a further object of the present invention is to provide a vapor generator and method of dispensing vapors from a liquid concentrate, such as deodorant-fragrance concentrate, wherein the dispensing rate is so well controllable that no evaporation retardant material is required to be included in the liquid formulations, and wherein formulations can thereby be provided to produce a desired extended operational life cycle regardless of variations in the particular active ingredient used or differences in fan speeds of fan dispensers wherein the vapor generators may be utilized.

A presently preferred form of vapor generator according to the invention employs a small pull-top type can as a receptacle for a liquid deodorant-fragrance concentrate that is adapted for the counteracting or replacing of undesirable odors. Crimped immediately underneath the pull-top of the can is an inner closure diaphragm of capillary action material such as blotter paper, non-woven fabric or the like which serves the dual functions of providing a positive barrier against spillage of any of the liquid contents of the can and providing a vapor dispensing diaphragm of accurately predetermined dimension. Disposed within the can and extending from the bottom of the can upwardly through its entire height into engagement with the said capillary action diaphragm is liquid transport means which, like the said diaphragm, is a capillary action membrane. This liquid transport capillary action means continuously supplies the said vapor dispensing diaphragm with the liquid concentrate regardless of how low the level of liquid concentrate becomes in the can, until the entire liquid contents of the can have been transported upwardly by capillary action through the transport means into the diaphragm and thence vaporized from the exposed surface of the diaphragm. A small pressure equalization port through the diaphragm prevents thermal vapor pressure buildup underneath the diaphragm and thereby prevents any interference with or interruption of the capillary action flow as result of pressure buildup. Otherwise, such vapor pressure buildup appears to retard the capillary action flow, and if the diaphragm were bowed too far upwardly by such internal pressure it could become separated from the upper edge of the liquid transport means and thereby produce a complete interruption in the capillary flow path.

The dispensing rate of the present invention is so well controlled and so uniform throughout the operational life cycle of the dispenser that the usual non-volatile vaporization retardant can be eliminated, whereby substantially the entire liquid contents of the dispenser can be vaporized from the dispensing diaphragm, leaving a substantially empty can with minimal disposal problems. This also permits formulations of liquid deodorant-fragrance concentrates to be provided which have substantially the same protracted operational life cycle despite differences in the fan speed of associated AC and DC fan dispensers. The desired formulation flexibility for accommodating different fragrance concentrates as active materials and for accommodating different fan speeds is permitted by mixing the concentrate with an inert carrier combination consisting of alcohol and odorless mineral spirits.

Other details, aspects and advantages of the present invention will be apparent from the following description taken in connection with the accompanying drawings, wherein:

BRIEF DESCRIPTION OF THE DRAWINGS

FIG. 5 is a vertical section taken on the line 5—5 in FIG. 4 illustrating internal details of construction of the vapor generator;

FIG. 6 is a top plan view of the activated vapor generator shown in FIGS. 4 and 5, with the internal liquid transport means shown in phantom;

FIG. 7 is a composite perspective view illustrating four different configurations of the liquid transport means; and FIGS. 8, 9 and 10 illustrate three different types of vapor dispensing diaphragms which may be employed to control the vapor dispensing rate, the diaphragms of FIGS. 8, 9 and 10 each having sections thereof which are insensitive to capillary action.

DETAILED DESCRIPTION

Figure 1:
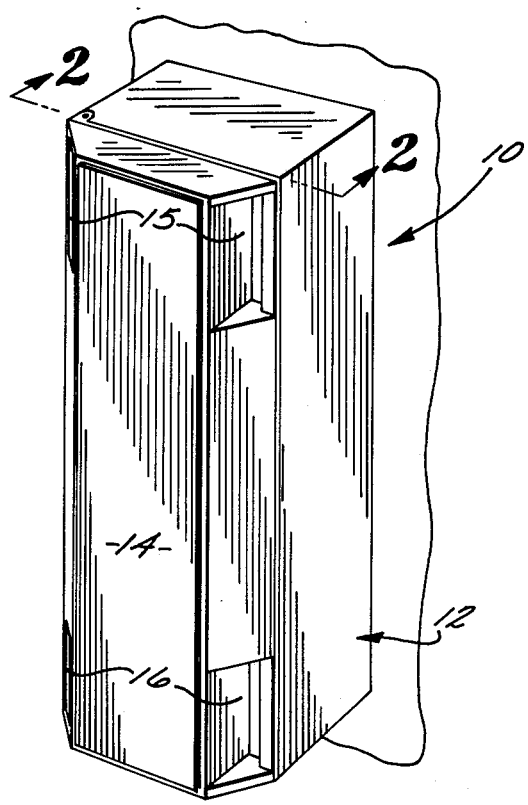
FIG. 1 is a perspective view of a fan dispenser within which a vapor generator according to the invention may be employed.
Figure 2:
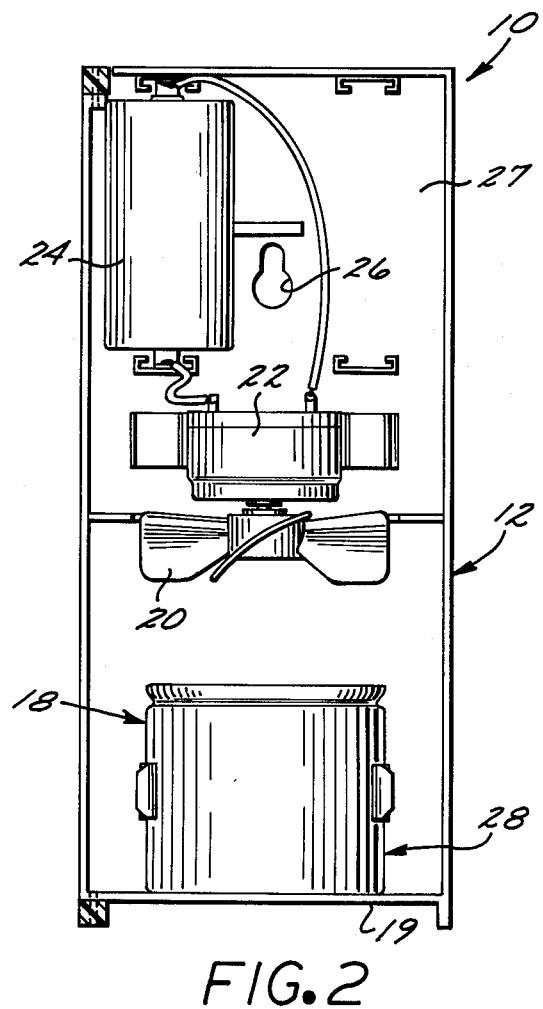
FIG. 2 is a vertical section taken on the line 2—2 in FIG. 1 showing the internal arrangement of the fan dispenser of FIG. 1 and placement of a vapor generator of the invention therein.
Figure 3:
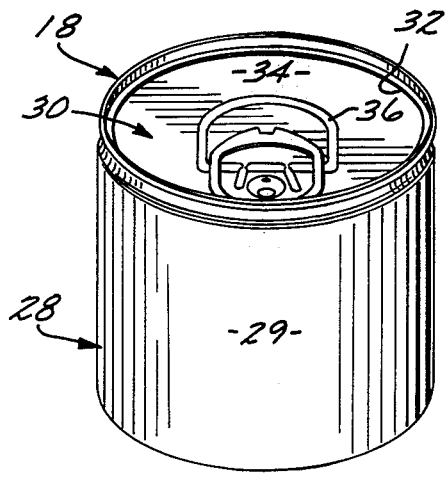
FIG. 3 is a perspective view of an unactivated vapor generator according to the invention.
Figure 4:
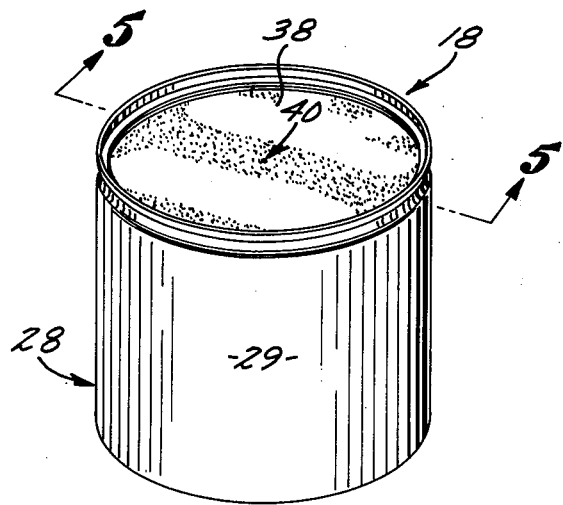
FIG. 4 is a perspective view similar to FIG. 3, but with the vapor generator activated by having removed the pull-top from the vapor generator.

Referring to the drawings, and at first to FIGS. 1 and 2 thereof, a fan dispenser generally designated 10 is preferably employed with the liquid vapor generator device of the present invention for best dispersion of the generated vapors about a region, such as a room, wherein the environment is to be controlled or treated. Fan dispenser 10 comprises a housing 12 having a pivotally openable front panel 14 with upper air inlet ports 15 and lower air outlet ports 16 therein.

As shown in FIG. 2, inside of the fan dispenser housing 12, a vapor generator device 18 according to the invention rests upon bottom wall 19 of fan dispenser housing 12, the vapor generator device 18 being adapted to dispense environmental control vapors at a controlled rate over an extended period of time, preferably in excess of 30 days. A fan 20 is positioned directly above vapor generator device 18 and is adapted to circulate air through the fan dispenser housing 12, the air being inducted into housing 12 through air inlet ports 15 proximate the top thereof, driven downwardly through the interior of housing 12 and over the top of vapor generator device 18 so that vapors dispensed from the generator device 18 will be picked up by this moving air, and thence out of housing 12 through air outlet ports 16 to be dispersed throughout the surrounding region. Fan 20 is driven by an electric motor 22 which is energized by battery means 24. An inverted keyhole 26 is provided in the back wall 27 of housing 12 to enable the fan dispenser 10 to be hung on a nail or hook on a wall. If desired, the fan dispenser 10 may simply be freestanding on a shelf of the like, particularly in view of the fact that even in the dispensing mode of the vapor generator device 18, the vapor generating liquid therein is completely enclosed and not susceptible to spilling if the apparatus is tampered with.

The fan dispenser 10 that is illustrated in FIGS. 1 and 2 is of the continuously operating DC type. However, it is to be understood that a fan dispenser may be employed that is AC energized, and that the fan dispenser may, if desired, be of the intermittently operating type. Examples of suitable fan dispensers for use with the present invention are those provided by Cline-Buckner, Inc. of Cerritos, Ca., Envair Inc. of San Antonio, Tx., Odorite of America of Kansas City, Mo., and Saniair, Inc. of Glenshaw, Pa.

Although the vapor generator device 18 of the present invention will normally be employed in a fan dispenser where wide dispersion of the vapors is desired, it is to be understood that there are many applications of the vapor generator device 18 where it may be employed without an accompanying fan dispenser for direct vapor dispensing into a region.

FIGS. 3-6 illustrate a presently preferred form of vapor generator device 18 according to the invention. The vapor generator 18 includes a receptacle 28 of a type having a removable lid. Preferably, the receptacle 28 is a small can of the pull-top type such as an aluminum "snack pack" can adapted to contain approximately five fluid ounces. Can 28 includes a generally cylindrical body 29 having a lid 30 with a peripheral score 32 therein defining the perimeter of a removable portion 34 of lid 30. A pull ring 36 is attached to removable lid portion 34. In the inoperative mode of condition of vapor generator 18 for storage and transport thereof, the can lid 30 will be intact, and the can 28 will be sealed. In order to activate the vapor generator 18 to its operative mode or condition for vapor dispensing, all that is required is to pull upwardly on the ring 36 so as to peel back and remove the removable lid portion 34.

Immediately beneath and parallel to the can lid 30 is an inner closure member 38 which serves as a dispensing diaphragm, the inner closure member 38 being exposed to the atmosphere upon removal of the removable lid portion 34 over the entire area circumscribed by the peripheral score 32. The inner closure member 38 is a capillary action membrane adapted to receive vapor generating liquid from another capillary action membrane in contact with a localized region thereof and transport the vapor generating liquid by capillary action over its entire disc so as dispense vapors to the atmosphere from its entire exposed upper surface defined within peripheral score 32. Where the vapor generating liquid has a petroleum base, as for example a base of odorless mineral spirits, blotter paper has been found to be a suitable material for the inner closure member 38. However, if the vapor generating liquid has a water base, then another type of capillary action membrane is preferred, such as non-woven fabric. A tiny hole 40 is provided through the center of inner closure member 38 which serves as a pressure relief port to prevent buildup of vapor pressure in the head space between the inner closure member 38 and the vapor generating liquid in receptacle 28 under elevated temperature conditions. Such buildup of vapor pressure under the inner closure member 38 has been found to have a tendency to interfere with capillary action that is employed within receptacle 28 for transporting the vapor generating liquid to the inner closure member 38 by means described in detail hereinafter.

The pressure relief port 40 need only be sufficiently large to relieve vapor pressure from underneath inner closure member 38. However, because of the tendency of the fibrous membrane forming the inner closure member 38 to swell and thereby tend to close the hole 40, it is preferred to provide the hole 40 in the range of from about 0.020 inch to 0.050 inch diameter. The hole 40 is, nevertheless, too small to permit any spillage of the vapor generating fluid, even if the receptacle 28 were to be turned upside down.

As best seen in FIGS. 5 and 6, the can lid 30 is peripherally connected to the upper edge of can body 29 by means of a crimp 42. When the crimp 42 is applied, the disc-shaped inner closure member 38 is peripherally crimped between the lid 30 and body 29 of can 28 so as to permanently secure the inner closure member 38 in its operative position. The inner closure member 38 is thus gripped between the peripheral portion 44 of lid 30 which lies outside of the score 32 and a radially inwardly directed annular flange or shelf 46 on the body 29.

A vapor generating liquid 48 is provided in the receptacle 28 which is adapted to produce the desired environmental control vapors. Although any vapor generating liquid 48 may be employed in the vapor generator 18, the vapor generator 18 has been found to be particularly useful for dispensing vapors from a deodorant-fragrance concentrate of the type adapted to counteract undesired odors. The vapor generating liquid 48 will be described more in detail hereinafter.

Liquid transport means 50 is arranged within receptacle 28 to extend from proximate the bottom of receptacle 28 upwardly through the entire height of receptacle 28 into direct physical contact with the lower surface of the inner closure member 38. Liquid transport means 50 is, like the inner closure member 38, a capillary action membrane, and in the embodiment illustrated in FIGS. 5 and 6 the liquid transport means 50 is in the form of a right circular cylinder. The top edge 52 of cylindrical transport means 50 directly abuts against the lower surface of inner closure member 38 about the entire circumference of edge 52 while the bottom edge 54 of cylinder 50 rests upon a flat chipboard bottom insert disc 56 which is employed to assure stability of the vertical positioning of cylinder 50 in view of the irregularly shaped bottom 58 usually found on a can of the type available for the receptacle 28. Both the inner closure member 38 and the chipboard insert disc 56 are substantially rigid, although either or both may be slightly flexed apart upon engagement of cylinder 50 therebetween to assure a compressive engagement of the top edge 52 of cylinder 50 against the inner closure member 38.

The liquid transport cylinder 50 may be composed of tubular cardboard stock if the vapor generating liquid 48 has a petroleum base, as for example odorless mineral spirits, but if the vapor generating liquid 48 has a water base it is preferred that the liquid transport cylinder 50 be composed of a substantially rigid woven fabric material.

In the inoperative mode or condition of the vapor generator 18, the can 28 will be completely sealed, so that no vapors are emitted. The can will be substantially full of the vapor generating liquid 48, as in FIG. 5, with both the liquid transport means 50 and the inner closure member 38 completely saturated with the vapor generating liquid 48. The vapor generator 18 is activated to its operative mode or condition by pulling upwardly on the ring 36 to disengage the removable portion 34 from the can lid 30, thereby exposing the upper surface of inner closure member 38 to the atmosphere, and since the inner closure member 38 is already completely saturated with vapor generating liquid 48, it will immediately serve as a vapor dispensing diaphragm of precise area which does not vary over the entire operative life of the device. Capillary action of both the liquid transport means 50 and the inner closure member 38 maintain the inner closure member 38 saturated as the level of the body of vapor generating liquid 48 goes down from the full condition all of the way to the substantially empty condition of receptacle 28, and the vapor dispensing rate of the diaphragm 38 is substantially constant during this entire operative life of vapor generator 18, which is of substantially predetermined duration, such as in excess of 30 days. Presence of the pressure relief port 40 to substantially equalize the pressure under the diaphragm 38 to atmospheric pressure assures that the capillarity of transport means 50 and diaphragm 38 remain essentially constant throughout this entire operative life of vapor generator 18.

The system of the present invention embodying the vapor dispensing diaphragm 38 of precise predetermined area dimension which is saturated with the vapor generating liquied 48 through the liquid transport means 50 by capillary action provides such good control over the rate of evaporation of the vapor generating liquid 48 that formulations for the vapor generating liquid 48 may be provided which have the desired operational life (e.g., more than 30 days), while at the same time the ingredients thereof may be selected to all evaporate approximately in proportion to their relative proportions by weight through the whole evaporation cycle, so that the composition dispensed in the air is substantially uniform throughout the operational cycle, and further so that substantially the entire quantity of vapor generating liquid 48 in the receptacle 28 will evaporate, leaving a dry can at the end of a complete cycle of operation. This greatly simplfies the disposal problem at the end of the cycle as compared with the up to 40% to 60% of retardant liquid hydrocarbons still remaining in the wick type vapor generator, and also enables a considerably larger amount of active ingredient to be dispensed for a given size vapor generator receptacle.

An example of a suitable formulation for the vapor generating liquid 48 where the active ingredient is cherry oil employed for odor control, where the vapor generator 18 is to be employed in a continuous DC type fan dispenser 10, is 70% active ingredient and 30% inert carrier, where the inert carrier comprises 20% isopropyl alcohol and 10% odorless mineral spirits. An example of suitable odorless mineral spirits is the aliphatic solvent Shell-Sol 72, obtainable from Shell Chemical Company, a division of Shell Oil Company of Houston, Tx. A cherry deodorant formulation for vapor generating liquid 48 employed in a vapor generator 18 adapted for use in a continuous AC fan dispenser 10 comprises 80% active ingredient and 20% inert carrier, the carrier comprising 15% isopropyl alcohol and 5% of the aforesaid odorless mineral spirits. The AC fan generates more wind, and hence the higher percentage of active ingredient is required to maintain the desired cycle of the unit despite the tendency for the increased wind to cause a greater rate of evaporation. The relative percentages of isopropyl alcohol and odorless mineral spirits are then adjusted between the DC and AC formulations of the vapor generating liquid so that the inert carrier in each case will evaporate at the same rate in proportion to its weight as the active ingredient, for a uniform rate of dispensing of the active ingredient and so that the entire vapor generating liquid content of receptacle 28 will disappear at the end of the operative cycle.

This adjustment of the relative percentages of isopropyl alcohol and odorless mineral spirits provides the inert carrier and the active ingredient with substantially isotropic vapor pressures; i.e., their boiling points are substantially the same at the same temperature, which causes the inert carrier and the active ingredient to boil off or evaporate in approximately their proportions. With the isotropic vapor pressures, the inert carrier and active ingredient molecules will be present at the dispensing surface of inner closure member 38 in approximately the same percentages as the formulation percentages of these ingredients.

The percentage proportions by weight of the vapor generating liquid 48 will be different for different fragrance compounds in order for the different vapor generating liquids 48 to have approximately the same operational time duration in vapor generator 18 and in order for the active ingredient and the inert carrier to evaporate substantially according to their respective proportions. Thus, for example, if vapor generating liquid 18 has lemon fragrance compound as its active ingredient, for the vapor generating liquid 48 to have an operative cycle in excess of 30 days, and evaporation to be proportional, a formulation for use with a continuous DC fan dispenser 10 contains 65% lemon fragrance compound, 20% isopropyl alcohol, and 15% of said odorless mineral spirits; while a formulation for use in a continuous AC fan dispenser 10 contains 73% lemon fragrance compound, 10% isopropyl alcohol and 17% of said odorless mineral spirits. As another example, using rose fragrance compound as the active ingredient, a formulation for vapor generating liquid 48 intended for use with a continuous DC fan dispenser 10 has 50% rose fragrance compound, 25% isopropyl alcohol and 25% of said odorless mineral spirits; while a formulation for use in a continuous AC fan dispenser has 61% rose fragrance compound, 15% isopropyl alcohol and 24% of said odorless mineral spirits.

It will be understood from the foregoing discussion of the vapor generating liquid 48 that one means for controlling or achieving a different vapor dispensing rate is to control or vary the relative proportions of the active ingredient and the inert carrier. Another means that may be employed for controlling or varying the vapor dispensing rate of the vapor generator 18 is to employ liquid transport means of modified configuration for transporting the vapor generating liquid 48 to the inner closure member 38 by capillary action. Referring to FIG. 7, four alternative liquid transport means configurations are there illustrated in a comparative display. The liquid transport means 50 is of right circular cylindrical configuration having an uninterrupted or unvaried top edge 52 which lies entirely within a common plane that is normal to the axis of the cylinder. The liquid transport means 50a shown in FIG. 7 is also a right circular cylinder, but its top edge 52 is of scalloped configuration, having alternate rises 60 and depressions 62 thereabout, so that only the rises 60 engage against the inner closure member 38. This reduces the capillary interface between the liquid transport means 50a and the inner closure member 38, thereby reducing the rate of transport of the vapor generating liquid 48 to inner closure member 38, and consequently reducing the rate of evaporation thereof from the inner closure member 38. Examples of other configurations for the liquid transport means illustrated in FIG. 7 are liquid transport means 50b which is a right cylinder of triangular cross section, and liquid transport means 50c which is a right cylinder of square cross section. It will be apparent to those skilled in the art that a variety of cross-sectional configurations may be employed in the liquid transport means, and the rate of capillary action transport thereby to the inner closure member 38 will vary according to the configuration.

FIGS. 8, 9 and 10 illustrate still another means for controlling or adjusting the vapor dispensing rate of the vapor generator 18. Thus, FIG. 8 illustrates, in plan view, a modified form of inner closure member or vapor dispensing diaphragm 38a wherein a series or regularly spaced, radially oriented wedge-shaped sections 64 of the diaphragm 38 are composed of a material that is substantially impervious to the vapor generating liquid 48; i.e., of a material which will not soak up the vapor generating liquid 48 by capillary action. These wedge-shaped sections 64 may be provided by saturation of the region 64 with a glue that is insensitive to the vapor generating liquid 48, or they may constitute separate wedge-shaped pieces of a different material. The alternate wedge-shaped regions 66 of the dispensing diaphragm 38a have capillary action capability, and are preferably composed of blotter paper, non-woven fabric, or the like.

Another array for controlling or adjusting the vapor dispensing rate is illustrated in FIG. 9, and comprises alternate parallel strips across the vapor dispensing diaphragm 38b, the strips 68 being insensitive to capillary action, and the strips 70 being capable of capillary action. A still further array for accomplishing this same control or adjustment is illustrated in FIG. 10, which shows a vapor dispensing diaphragm 38c having capillarity-insensitive inner disc and outer ring portions 72 and 74, respectively, and an intermediate ring section 76 capable of capillary action. It is to be noted that a common characteristic of all of the vapor dispensing diaphragms, including the basic uninterrupted diaphragm 38, the diaphragm 38a of FIG. 8 having the radially directed insensitive wedges, the diaphragm 38b of FIG. 9 having the parallel insensitive strips, and the diaphragm 38c of FIG. 10 having the insensitive annular areas, is that the capillarity sensitive areas on each of these diaphragm embodiments are arranged to be suitable for engagement by a cylindrical shaped liquid transport means of a desired cross-sectional configuration and of suitable cross-sectional dimensions.

While the invention has been described with reference to the above disclosure relating to the preferred embodiments, it is understood that numerous modifications or alterations may be made of those skilled in the art without departing from the scope and spirit of the invention as set forth in the appended claims.

I claim:

1. A vapor generator which comprises:
    closed receptacle means having an openable top portion.
    capillary action diaphragm means in the upper portion of said receptacle means beneath said openable top portion and adapted to have one side thereof exposed upon opening of said top portion,
    vaporizable liquid concentrate in said receptacle means below said diaphragm means, and
    liquid transport means in said receptacle means below said diaphragm means, said transport means engaging said diaphragm means and extending downwardly therefrom into said liquid concentrate,
    said transport means being adapted to transport said liquid concentrate to said diaphragm means for vaporization thereof from said exposed side of said diaphragm means,
    said receptacle means comprising a can having a lid with a peripheral scare defining a removable central portion and a peripheral portion which remains after removal of said central portion,
    said diaphragm means extending across the aperture remaining in said lid after removal of said central portion, and
    said diaphragm means having a peripheral portion which is supported in said can beneath said peripheral portion of said lid.

2. A vapor generator as recited in claim 1, wherein said receptacle means comprises a pull-top can.

3. A vapor generator as recited in claim 1, wherein said diaphragm means has a pressure equalization port extending therethrough.

4. A vapor generator as recited in claim 3, wherein said pressure equalization port is generally centrally located in said diaphragm means.

5. A vapor generator as recited in claim 3, wherein said pressure equalization port has a diameter not larger than about 0.050 inch.

6. A vapor generator as recited in claim 1, wherein said diaphragm means comprises blotter paper.

7. A vapor generator as recited in claim 1, wherein said diaphragm means comprises non-woven cloth.

8. A vapor generator as recited in claim 1, wherein said liquid transport means comprises capillary action means.

9. A vapor generator as recited in claim 8, wherein said liquid transport means comprises cardboard.

10. A vapor generator as recited in claim 8, wherein said liquid transport means comprises non-woven cloth.

11. A vapor generator as recited in claim 8, wherein said liquid transport means has upper end means engaged with said diaphragm means and extends downwardly through said receptacle means to lower end means located proximate the bottom of said receptacle means.

12. A vapor generator as recited in claim 11, wherein said liquid transport means is substantially tubular.

13. A vapor generator as recited in claim 12, wherein said liquid transport means is generally circularly cylindrical.

14. A vapor generator as recited in claim 12, wherein said liquid transport means comprises a cardboard tube.

15. A vapor generator as recited in claim 11, wherein said upper end means comprises narrow, elongated, substantially uninterrupted upper edge means engaged with said diaphragm means.

16. A vapor generator as recited in claim 11, wherein said upper end means comprises narrow, elongated upper edge means which has a sequence of rises and depressions thereon to reduce its area of engagement with said diaphragm means.

17. A vapor generator as recited in claim 11, wherein a portion of at least said exposed side of said diaphragm means is insensitive to capillary action, thereby reducing the effective vaporization area of said exposed side of said diaphragm means.

18. A vapor generator as recited in claim 1, wherein said vaporizable liquid comprises fragrance concentrate as an active ingredient.

19. A vapor generator as recited in claim 18, wherein said vaporizable liquid comprises an inert carrier liquid, said active and carrier liquids having substantially isotropic vapor pressures.

20. A vapor generator as recited in claim 18, wherein said vaporizable liquid comprises an inert carrier liquid comprising alcohol and odorless mineral spirits.

21. A vapor generator as recited in claim 1, which comprises a fan dispenser within which said receptacle means is disposed with said openable top portion in its open position.

* * * * *

UNITED STATES PATENT AND TRADEMARK OFFICE
CERTIFICATE OF CORRECTION

PATENT NO. : 4,173,604

DATED : November 6, 1979

INVENTOR(S) : Dimitrios A. Dimacopoulos

It is certified that error appears in the above—identified patent and that said Letters Patent is hereby corrected as shown below:

Column 9, line 66, "scare" should read -- score --.

Signed and Sealed this

First Day of September 1981

[SEAL]

Attest:

GERALD J. MOSSINGHOFF

*Attesting Officer*     *Commissioner of Patents and Trademarks*